(12) United States Patent
Binier (10) Patent No.: US 9,545,482 B2
(45) Date of Patent: Jan. 17, 2017

(54) DRUG INFORMATION DETECTION DEVICE AND DRUG INFORMATION DETECTION TYPE INJECTION DEVICE

(71) Applicant: INNOVATIVE PRECISION INSTRUMENTS LIMITED, Hong Kong OT (HK)

(72) Inventor: Richard Jean Marie Binier, Hong Kong (HK)

(73) Assignee: Innovative Precision Instruments Limited, Hong Kong (HK)

( * ) Notice: Subject to any disclaimer, the term of this patent is extended or adjusted under 35 U.S.C. 154(b) by 0 days.

(21) Appl. No.: 15/194,012

(22) Filed: Jun. 27, 2016

(65) Prior Publication Data
US 2016/0303326 A1   Oct. 20, 2016

(30) Foreign Application Priority Data

Mar. 3, 2015   (CN) .................................. 104800932
Nov. 20, 2015  (WO) ................ PCT/CN2015/073577

(51) Int. Cl.
*A61M 3/00*      (2006.01)
*A61M 5/315*     (2006.01)
(Continued)

(52) U.S. Cl.
CPC ............. *A61M 5/3155* (2013.01); *A61M 5/00* (2013.01); *A61M 5/31* (2013.01); *A61M 5/31585* (2013.01);
(Continued)

(58) Field of Classification Search
CPC ............ A61M 5/3155; A61M 5/31585; A61M 2205/3576; A61M 2205/8206; A61M 2209/04; A61M 2205/52; A61M 2005/3126; A61M 5/31525; A61M 5/31551; A61M 5/31568; A61M 5/31535; A61M 5/31553; A61M 5/3158; G01D 5/12; G01D 5/2451; G01D 5/2497; G06F 19/3468; G06F 19/3406
(Continued)

(56) References Cited

U.S. PATENT DOCUMENTS 8,221,356 B2   7/2012 Enggaard
8,465,448 B2   6/2013 Garcia De Castro Andrews
(Continued)

FOREIGN PATENT DOCUMENTS

CN   101862489 A   10/2010
CN   102413856 A   4/2012
(Continued)

*Primary Examiner* — Jason Flick
(74) *Attorney, Agent, or Firm* — Kramer & Amado, P.C.

(57) ABSTRACT

The present invention relates to a field of drug injection, and discloses a drug information detection device and a drug information detection type injection device. The drug information detection device is configured to detect an injected dose of an injection pen containing drug. The drug information detection device includes a housing, a rotary encoder configured to convert rotational information of the adjusting knob into drug injected dose information, and a control assembly. The rotary encoder includes an encoder body and a rotary block rotatably connected to the encoder body. The encoder body and the control assembly are electrically connected to each other. The housing is configured to cover the encoder body and the control assembly.

11 Claims, 3 Drawing Sheets

(51) Int. Cl.
*A61M 5/00* (2006.01)
*A61M 5/31* (2006.01)
*G06F 19/00* (2011.01)
*G01D 5/12* (2006.01)

(52) U.S. Cl.
CPC ............... *G01D 5/12* (2013.01); *G06F 19/00* (2013.01); *A61M 2205/3576* (2013.01); *A61M 2205/8206* (2013.01); *A61M 2209/04* (2013.01)

(58) Field of Classification Search
USPC ........................................................ 604/189
See application file for complete search history.

(56) References Cited

U.S. PATENT DOCUMENTS

| | | | |
|---|---|---|---|
| 8,556,866 B2 | 10/2013 | Krulevitch et al. | |
| 8,961,463 B2 | 2/2015 | Edhouse et al. | |
| 9,186,465 B2 | 11/2015 | Jorgensen et al. | |
| 9,192,728 B2 | 11/2015 | Gilmore | |
| 9,314,573 B2 | 4/2016 | Nielsen et al. | |
| 2008/0188813 A1 | 8/2008 | Miller et al. | |
| 2008/0243088 A1 | 10/2008 | Evans | |
| 2011/0313349 A1* | 12/2011 | Krulevitch | A61M 5/24 604/65 |
| 2012/0065588 A1 | 3/2012 | Cirillo et al. | |
| 2014/0121602 A2 | 5/2014 | Ning et al. | |
| 2014/0194825 A1 | 7/2014 | Nielson | |
| 2014/0194826 A1 | 7/2014 | Nielsen et al. | |
| 2014/0194829 A1* | 7/2014 | Baek | A61M 5/31551 604/207 |
| 2015/0018775 A1 | 1/2015 | Groeschke et al. | |
| 2015/0112272 A1 | 4/2015 | Wendland | |
| 2015/0190583 A1 | 7/2015 | Jones | |
| 2015/0202375 A1 | 7/2015 | Schabbach et al. | |
| 2015/0343152 A1 | 12/2015 | Butler et al. | |
| 2015/0367077 A1 | 12/2015 | Plambech et al. | |
| 2016/0001011 A1 | 1/2016 | Cammish et al. | |
| 2016/0008552 A1 | 1/2016 | Madsen | |
| 2016/0015903 A1 | 1/2016 | Madsen | |

FOREIGN PATENT DOCUMENTS

| | | |
|---|---|---|
| CN | 102427840 A | 4/2012 |
| CN | 102526833 A | 7/2012 |
| CN | 103702699 A | 4/2014 |
| CN | 204411425 U | 6/2015 |
| EP | 0554996 A1 | 11/1993 |
| EP | 2011531 A2 | 3/2004 |
| EP | 2364742 A2 | 9/2011 |
| EP | 2427236 B1 | 1/2014 |
| TW | 201107004 A | 3/2011 |
| TW | 201402164 A | 1/2014 |
| TW | 201534364 A | 9/2015 |
| WO | 2010139632 A2 | 12/2010 |
| WO | 2012152628 A1 | 11/2012 |
| WO | 2013004844 A1 | 1/2013 |
| WO | 2013164291 A1 | 11/2013 |

\* cited by examiner

DRUG INFORMATION DETECTION DEVICE AND DRUG INFORMATION DETECTION TYPE INJECTION DEVICE

BACKGROUND OF THE INVENTION

Field of the Invention

Various embodiments disclosed herein generally relate to a field of drug injection, and more particularly, to a drug information detection device and a drug information detection type injection device.

Description of Related Art

In the prior art, an injection pen (such as an insulin injection pen) is provided for allowing a patient to select a dose and perform self-injection, such that the patient with chronic disease can perform self-treatment at home.

Generally, the injection pen comprises an injection part and a detection part configured to determine a dose. The injection part comprises a barrel configured to contain drugs, and a plunger. The detection part comprises a sleeve and an adjusting knob, wherein the sleeve is fixed to the barrel and has graduation marks. The adjusting knob is rotatably connected to one end of the sleeve through a screw thread. The plunger passes through the sleeve and is connected to the adjusting knob. Before injection, the adjusting knob is rotated to drive the plunger to move until the adjusting knob reaches a predetermined graduation mark on the sleeve. As such, the movement of the plunger is determined, and a proper drug dose is selected. Thereafter, the adjusting knob is pushed to drive the plunger to move down, so as to push the drug out of the barrel for completing injection.

The injection pen of the prior art can select drug dose, but information of injection time, amounts of injected doses, number of injections cannot be recorded by the injection pen of the prior art. The above information is very important to the patient for treatment. It is a very important diagnosis reference to a doctor. Without recording related information, the patient may forget the injection time and the number of injections, so as to inject too many or too few times, thus disease gets worse.

In order to record the drug injection information of the injection pen, the prior art utilizes a detection device matched with or integrated to the injection pen. The detection device mostly uses a sensor or optical recognition to detect the moving distance of the plunger, and convert a detection result into an electronic data. Since a computation result is directly affected by detection of the moving distance of the plunger. The detection device requires higher accuracy for installation, needs to perform complex operations during detection, and may easily cause detection error, such that the detection device of the prior art cannot meet user's recording requirement.

SUMMARY OF THE INVENTION

The present invention provides a drug information detection device in order to solve problems of the prior art, where a detection device of the prior art requires higher accuracy for installation, needs to perform complex operations during detection, and may easily cause detection error.

The drug information detection device of the present invention is configured to detect an injected dose of an injection pen containing drug. An adjusting knob is arranged at one end of the injection pen for determining the injected dose. The drug information detection device comprises a housing, a rotary encoder configured to convert rotation information of the adjusting knob into drug injected dose information, and a control assembly. The rotary encoder comprises an encoder body and a rotary block rotatably connected to the encoder body. The encoder body and the control assembly are electrically connected to each other and are fixed to the adjusting knob. The housing is configured to cover the encoder body and the control assembly. A button is arranged at a first end of the housing. The rotary block is fixedly connected to the button.

Further, the control assembly comprises a wireless transmission module configured to transmit information wirelessly.

Further, the encoder and the control assembly are fixed in the housing. A second end of the housing is fixed to the adjusting knob. The button is rotatably connected to the first end of the housing.

Further, a retaining ring is arranged at the first end of the housing. A first end of the button passes through the retaining ring. A limit ring is arranged at an outer edge of a second end of the button for engaging with the retaining ring.

In contrast to the prior art, the drug information detection device of the present invention is directly installed on the adjusting knob of the injection pen. When performing injection, a user pushes the button to press down the drug information detection device. A pressing force is transmitted to the adjusting knob. The adjusting knob converts the pressing force into a rotating force, and then rotates and descends in order to drive the encoder body to rotate. Since the rotary block is connected to button, the rotary block does not rotate when the button is continuously pushed. Therefore, the rotary block can stay still during injection, and the encoder body rotates relative to the rotary block. The encoder body detects a rotation amount of the encoder body relative to the rotary block, which is equal to a rotation amount of the adjusting knob. The rotation amount is converted into injected dose information and stored in the control assembly. Accordingly, a drug information detection process is completed. When the drug information detection device of the present invention performs detection to the injection pen, no additional detection operation is required and the drug information detection device is easy to operate. During installation, an internal structure of the drug information detection device needs only to be arranged for rotating simultaneously with the adjusting knob. Therefore, the drug information detection of the present invention requires lower accuracy for installation, and has less detection error.

The present invention further provides a drug information detection type injection device. The drug information detection type injection device comprises an injection pen having one end arranged with an adjusting knob and the aforementioned drug information detection device. The encoder body and the control assembly of the drug information detection device are fixed to the adjusting knob.

Further, a connection sleeve is arranged at one end of the adjusting knob. The second end of the housing is fixed to the connection sleeve through a screw thread. An accommodating chamber is formed inside the connection sleeve and the housing. The rotary encoder and the control assembly are arranged in the accommodating chamber.

Further, a battery is arranged in the accommodating chamber for providing power.

Further, a vibrator is arranged in the accommodating chamber and is controlled by the control assembly.

Further, a ring-shaped indicating lamp is arranged outside the connection sleeve and is controlled by the control assembly.

The drug information detection type injection device of the present invention integrates the aforementioned drug information detection device and the injection pen, for providing functions of injecting drug and detecting drug information. Operations of the drug information detection type injection device of the present invention is identical to those of an injection pen of the prior art. Therefore, no additional detection operation is required. During injection, drug information can be simultaneously collected, and the operation for collecting data is easy and has less error.

These and other objectives of the present invention will no doubt become obvious to those of ordinary skill in the art after reading the following detailed description of the preferred embodiment that is illustrated in the various figures and drawings.

The foregoing objects and advantages of the invention are illustrative of those that can be achieved by the various exemplary embodiments and are not intended to be exhaustive or limiting of the possible advantages which can be realized. Thus, these and other objects and advantages of the various exemplary embodiments will be apparent from the description herein or can be learned from practicing the various exemplary embodiments, both as embodied herein or as modified in view of any variation that may be apparent to those skilled in the art. Accordingly, the present invention resides in the novel methods, arrangements, combinations, and improvements herein shown and described in various exemplary embodiments.

BRIEF DESCRIPTION OF THE DRAWINGS

The accompanying figures, where like reference numerals refer to identical or functionally similar elements throughout the separate views, together with the detailed description below, are incorporated in and form part of the specification, and serve to further illustrate embodiments of concepts that include the claimed invention, and explain various principles and advantages of those embodiments.

These and other more detailed and specific features of the present invention are more fully disclosed in the following specification, reference being had to the accompanying drawings, in which.

The apparatus components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DETAILED DESCRIPTION OF THE PREFERRED EMBODIMENTS

Figure 1:
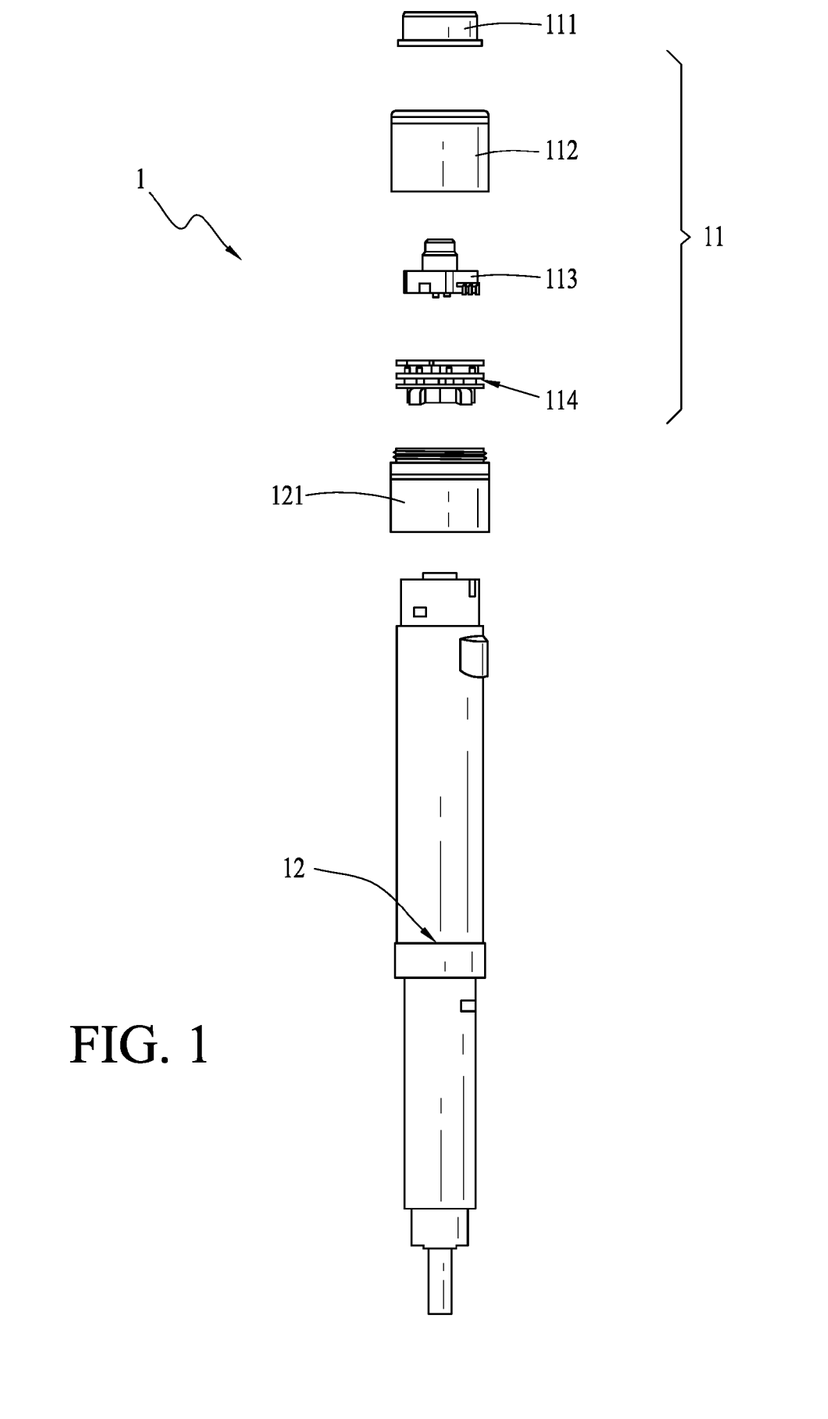
FIG. 1 is an exploded view of a drug information detection type injection device of the present invention.
Figure 2:
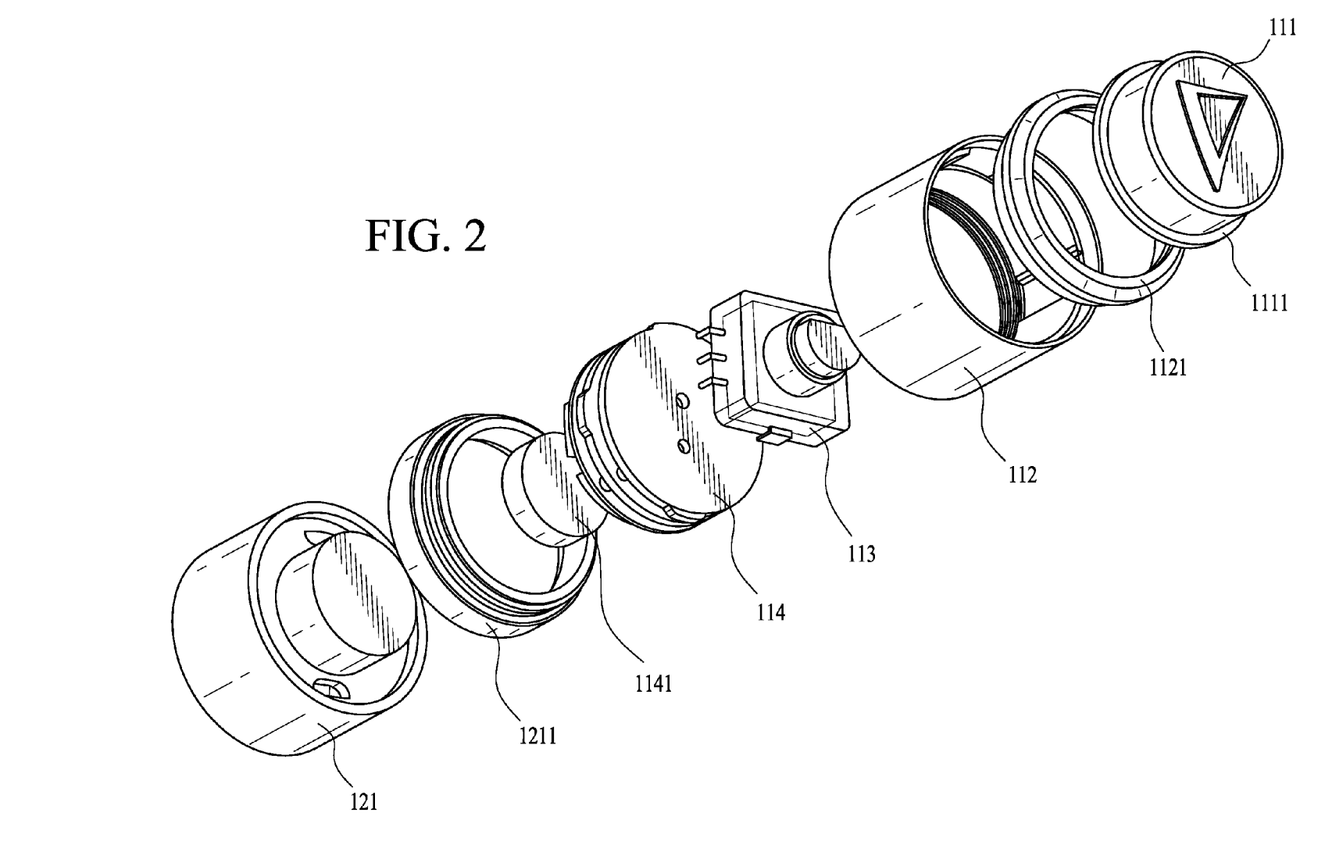
FIG. 2 is an exploded view of a drug information detection device and an adjusting knob of the present invention.

As shown in FIG. 1 and FIG. 2, a drug information detection device 11 comprises a housing 112, a rotary encoder 113 and a control assembly 114. Wherein, the housing 112 is cylindrical and covers the rotary encoder 113 and the control assembly 114. A button 111 is arranged at outside of a first end of the housing 112.

Figure 3:
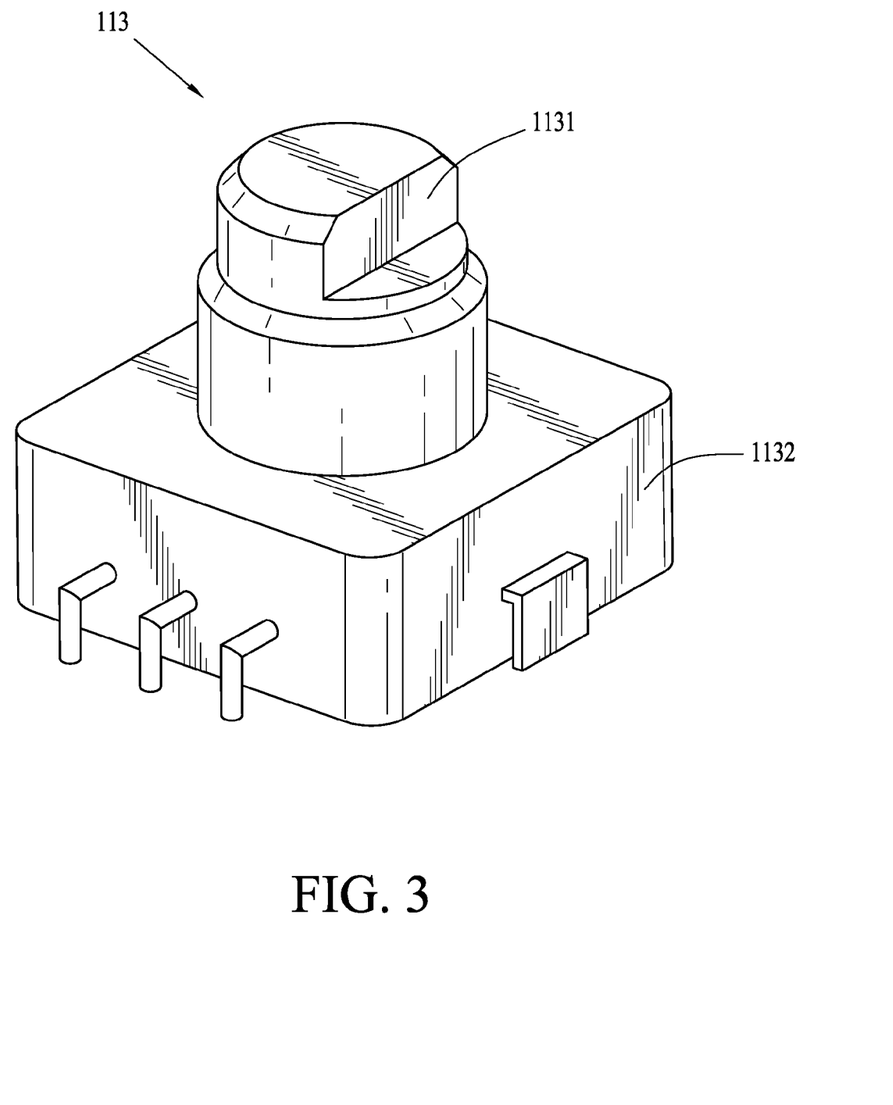
FIG. 3 is a diagram showing a rotary encoder.

As shown in FIG. 2 and FIG. 3, the rotary encoder 113 comprises an encoder body 1132 and a rotary block 1131 rotatably connected to the encoder body 1132. The rotary block 1131 is connected to the button 111. The encoder body 1132 and the control assembly 114 are electrically connected to each other, and fixed to an adjusting knob 121 of a injection pen 12 to rotate with the adjusting knob 121. When a user pushes the button 111, a force is transmitted from the button 111 to the rotary encoder 113 and further transmitted to the adjusting knob 121. When the adjusting knob 121 is pressed, the adjusting knob 121 rotates and moves downward in order to drive the encoder body 1132 to rotate simultaneously. Processes of the entire movement comprises the following steps: the user applying a force to the button 111; the button 111 driving the adjusting knob 121 to move downward together; the adjusting knob 121 driving the drug information detection device 11 to move downward with the encoder body 1132 rotating with the adjusting knob 121; and the adjusting knob 121 returning to an original limit position for completing the injection.

When using the drug information detection device 11 of the present invention, the drug information detection device 11 is first installed to the injection pen 12 to ensure that the encoder body 1132 and the control assembly 114 are fixed to the adjusting knob 121. When the user uses the injection pen 12 for injection, the user rotates the adjusting knob 121 to a required graduation mark and then pushes the button 111. Through the aforementioned force transmission processes, the adjusting knob 121 rotates and moves downward in order to drive a plunger of the injection pen 12 to move downward for completing the injection.

During the injection, the user continues pushing the button 111. The button 111 contacted with a finger of the user does not rotate, and the rotary block 1131 fixed to the button 111 does not rotate either. When the adjusting knob 121 is pressed to rotate and move downward for injection, the encoder body 1132 is simultaneously driven to rotate relative to the rotary block 1131. A rotation amount of the encoder body 1132 is equal to a rotation amount of the adjusting knob 121. The encoder body 1132 detects the relative rotation amount between the encoder body 1132 and the rotary block 1131, and converts the relative rotation amount into electronic data. The electronic data is further converted into drug dose data by the control assembly 114 to be recorded. The control assembly 114 simultaneously records the injection time.

Therefore, the drug information detection device 11 according to the present embodiment detects and stores the drug injected dose by using the rotary encoder 113 to detect the rotation amount of the adjusting knob 121. No sensor is required to detect a movement of the plunger, such that accuracy required for installation is lower. The user only needs to follow original operations of the injection pen 12 to rotate and push, no additional specific detection operation is required. The drug information detection device 11 converts the detected rotation amount into the drug injected dose, thus detection error is not easily occurred. The drug information detection device 11 has higher detection accuracy.

The control assembly 114 of the drug information detection device 11 of the present invention further comprises a wireless transmission module. The drug information (such as injected dose, injection time, etc.) stored in the control assembly can be transmitted to an external data processing device (such as a tablet computer, a mobile phone, a calculator, a router, etc.) through the wireless transmission module. In practical use, the wireless transmission module can be a Bluetooth module to communicate with a mobile terminal, such as a mobile phone or a tablet computer, for transmitting data periodically or in real time. The drug information can be recorded in the mobile terminal to be shown as diagrams or curves, so to intuitively remind a patient of drug usage. The wireless transmission module can also be a WIFI module to connect to Internet through a router, and directly transmit the drug information to a computer of a doctor at a remote site. Therefore, the doctor can remotely monitor the drug usage of the patient for a diagnosis basis.

The control assembly 114 of the drug information detection device 11 of the present invention further comprises a predetermined dose switching module, which is configured to switch data collection modes of the control assembly 114. After using the predetermined dose switching module, the control assembly 114 can record the drug injected dose of the injection pen and record the injection time as well.

There are different ways to fix the encoder body 1132 and the control assembly 114 to the adjusting knob 121. For example, for directly fixing the encoder body 1132 and the control assembly 114 to the adjusting knob 121, a fixing rack can be arranged for fixing the encoder body 1132 and the control assembly 114 to the fixing rack. A clamping structure can be arranged on the fixing rack for clamping the adjusting knob 121. When the adjusting knob 121 rotates, only the fixing rack, the encoder body 1132 and the control assembly 114 rotate with the adjusting knob 121, and the housing 112 stays still. In addition, for indirectly fixing the encoder body 1132 and the control assembly 114 to the adjusting knob 121, the encoder body 1132 and the control assembly 114 can be fixed in the housing 112, wherein the housing 112 is fixed to the adjusting knob 121. When the adjusting knob 121 rotates, the housing 112, the encoder body 1132 and the control assembly 114 rotate synchronously. As shown in FIG. 1 and FIG. 2, the embodiment uses the indirect way. The encoder body 1132 and the control assembly 114 are fixed in the housing. A second end of the housing 112 is fixed to the adjusting knob 121 to rotate with the adjusting knob 121. The button 111 is rotatably connected to the first end of the housing 112. When the button 111 is pushed for injection, the adjusting knob 121 drives the housing 112 to rotate. Since the button 111 is rotatably connected to the housing 112, the button 111 stays still and does not rotate with the adjusting knob 121. In the way of fixing the housing 112 to the adjusting knob 121, the housing 112 is integrated with the encoder body 1132 and the control assembly 114 in order to provide protection for components in the housing 112.

There are different ways to fix the housing 112 to the adjusting knob 121. For example, an adhesive structure can be arranged at an edge of the housing 112, such that the housing 112 can be adhered and fixed to the adjusting knob 121 when installing the drug information detection device 11. Or a plurality of screwing bolts can be arranged to surround an upper ring of the housing 112, such that when the housing 112 is sleeved on the adjusting knobs 121, the housing 112 can be screwed with the screwing bolts for fixing to the adjusting knob 121 during the installation. Other structures can be also used to fix the housing 112 to the adjusting knob 121, therefore, no further illustration is provided. The housing 112 can be fixed to the adjusting knob 121 for rotating synchronously in a simple and easy way.

There are different ways to rotatably connect the housing 112 and the button 111. In the present embodiment, a retaining ring 1121 is arranged at the first end of the housing 112. A first end of the button 111 passes through the retaining ring 1121, and a second end of the button 111 is arranged with a limit ring 1111 for engaging with the retaining ring 1121 in order to prevent the button 111 from detaching from the housing 112. When using the drug information detection device 11, the user pushes the button 111 and the button 111 moves downward to detach the limit ring 1111 from the retaining ring 1121. No friction is generated between the housing 112 and the button 111 while the housing 112 is driven to rotate by the adjusting knob 121. Therefore, the rotation is smoother. Moreover, the problem of the accuracy of the encoder body 1132 collecting relative rotation amount data being affected by an axial rotation of the rotary block 1131 due to rotation of the button 111 can be prevented. In practical use, other rotatable connection methods can be also used, such as using a rotary bearing to connect the housing 112 and the button 111.

The drug information detection device 11 according to the present embodiment can be installed on all kinds of injection pens 12 in the market. The drug information detection device 11 can be used to cooperate with the injection pen 12, for detecting drug injection information of the injection pen 12 and transmitting the drug injection information to the external device without additional operations. Therefore, the drug information detection device 11 provides convenience to users and doctors and has advantages of easy installation and operation, and high detection accuracy.

As shown in FIG. 1, the present embodiment further provides a drug information detection type injection device 1 which is formed by integrating the injection pen 12 with the drug information detection device 11. The adjusting knob 121 of the injection pen 12 is fixed to the encoder body 112 and the control assembly 114.

The drug information detection type injection device 1 of the present embodiment follows the same operations of the injection pen 12 in the market, such as rotating and pushing to complete the entire process of dose selection, injection, and drug information detection. The drug information detection type injection device 1 not only can adjust and select a dose for drug injection but also can automatically detect and store the drug injected dose information and the injection time, in order to provide an important diagnosis basis to the users and the doctors.

As shown in FIG. 1, a connection sleeve 1211 is arranged at one end of the adjusting knob 121. An outer side of the connection sleeve 1211 is arranged with a screw thread. The second end of the housing 112 is fixed to the connection sleeve 1211 through the screw thread. That is, the adjusting knob 121 and the housing 112 are fixed to each other through the connection sleeve 1211. An accommodating chamber is formed inside the connection sleeve 1211 and the housing 112. The rotary encoder 113 and the control assembly 114 are arranged in the accommodating chamber and fixed to the connection sleeve 1211 or the housing 112, such that the encoder body 1132 and the control assembly 114 can be driven to synchronously rotate with the adjusting knob 121.

Other circuit structures are arranged in the accommodating chamber. As shown in FIG. 2, the circuit structures include a battery (not shown in the figure) and a vibrator 1141. The battery is configured to provide power to the entire drug information detection device 11. The vibrator 1141 is controlled by the control assembly 114 and configured to vibrate at designated time or in a certain condition to remind the user. For example, scheduled injection time can be set in the vibrator 1141, such that the vibrator 1141 can vibrate for reminding the user.

In order to enhance the reminding function, a ring-shaped indicating lamp (not shown in the figure) can be arranged outside the connection sleeve 1211. The ring-shaped indicating lamp is controlled by the control assembly 114 and configured to blink at designated time or in a certain condition in order to cooperate with the vibrator 1141 for visually reminding the user. For example, the ring-shaped indicating lamp continues lighting during the injection, and turns to a blinking state when the injection is about to complete. The ring-shaped indicating lamp can display electricity capacity, an information transmission status, a wireless connection status, a drug information collection mode, etc. through different colors or frequencies of light, so as to work in different statuses according to requirements.

Those skilled in the art will readily observe that numerous modifications and alterations of the device and method may be made while retaining the teachings of the invention.

Accordingly, it is to be understood that the above description is intended to be illustrative and not restrictive. Many embodiments and applications other than the examples provided would be apparent upon reading the above description. The scope should be determined, not with reference to the above description or Abstract below, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the application is capable of modification and variation.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

All terms used in the claims are intended to be given their broadest reasonable constructions and their ordinary meanings as understood by those knowledgeable in the technologies described herein unless an explicit indication to the contrary in made herein. In particular, use of the singular articles such as "a," "the," "said," etc. should be read to recite one or more of the indicated elements unless a claim recites an explicit limitation to the contrary.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A drug information detection device configured to detect an injected dose of an injection pen containing drug, an adjusting knob being arranged at one end of the injection pen for determining the injected dose, the drug information detection device comprising:
   a housing;
   a control assembly;
   a rotary encoder configured to convert rotational information of the adjusting knob into drug injected dose information, the rotary encoder comprising:
      an encoder body;
      a rotary block rotatably connected to the encoder body, wherein
         the encoder body and the control assembly are electrically connected to each other,
         the housing covers the encoder body and the control assembly, a button is arranged at a first end of the housing,
         the rotary block is fixed to the button and wherein the encoder body and the control assembly are fixed in the housing,
         the button is rotatably connected to the first end of the housing,
         a retaining ring is arranged at the first end of the housing,
         a first end of the button passes through the retaining ring, and
         a limit ring is arranged at an outer edge of a second end of the button for engaging with the retaining ring.

2. The drug information detection device of claim 1, wherein the control assembly comprises a wireless transmission module configured to wirelessly transmit the drug injected dose information.

3. The drug information detection device of claim 1, further comprising:
   a connection sleeve, arranged at a first end of the adjusting knob, a second end of the housing is fixed to the connection sleeve through a screw thread, an accommodating chamber is formed inside the connection sleeve and the housing, and the rotary encoder and the control assembly are arranged in the accommodating chamber.

4. The drug information detection device of claim 3, wherein a battery is arranged in the accommodating chamber.

5. The drug information detection device of claim 3, wherein a vibrator is arranged in the accommodating chamber and controlled by the control assembly.

6. The drug information detection device of claim 3, wherein an indicating lamp is arranged on the outside of the connection sleeve and controlled by the control assembly.

7. A drug information detection type injection device, comprising:
   an injection pen having a first end arranged with an adjusting knob; and
   the drug information detection device comprising:
      a housing;
      a control assembly;
      a rotary encoder configured to convert rotational information of the adjusting knob into drug injected dose information, the rotary encoder comprising:
         an encoder body;
         a rotary block rotatably connected to the encoder body, wherein
            the encoder body and the control assembly are electrically connected to each other and fixed to the adjusting knob,
            the housing covers the encoder body and the control assembly, a button is arranged at a first end of the housing,
            the rotary block is fixed to the button and wherein the encoder body and the control assembly are fixed in the housing,
            the button is rotatably connected to the first end of the housing,
            a retaining ring is arranged at the first end of the housing, a first end of the button passes through the retaining ring, and
a limit ring is arranged at an outer edge of a second end of the button for engaging with the retaining ring.

8. The drug information detection type injection device of claim 7, further comprising:
a connection sleeve, arranged at a first end of the adjusting knob, a second end of the housing is fixed to the connection sleeve through a screw thread, an accommodating chamber is formed inside the connection sleeve and the housing, and the rotary encoder and the control assembly are arranged in the accommodating chamber.

9. The drug information detection type injection device of claim 8, wherein a battery is arranged in the accommodating chamber.

10. The drug information detection type injection device of claim 8, wherein a vibrator is arranged in the accommodating chamber and controlled by the control assembly.

11. The drug information detection type injection device of claim 8, wherein an indicating lamp is arranged on the outside of the connection sleeve and controlled by the control assembly.

* * * * *

UNITED STATES PATENT AND TRADEMARK OFFICE
CERTIFICATE OF CORRECTION

PATENT NO. : 9,545,482 B2  
APPLICATION NO. : 15/194012  
DATED : January 17, 2017  
INVENTOR(S) : Richard Jean Marie Binier Page 1 of 1

It is certified that error appears in the above-identified patent and that said Letters Patent is hereby corrected as shown below:

On the Title Page

1. Add item (63):
Related U.S. Application Data
Continuation of application No. PCT/CN2015/073577 filed on March 3, 2015

2. Delete item (30) Foreign Priority Data

Signed and Sealed this
Twentieth Day of November, 2018

Andrei Iancu
*Director of the United States Patent and Trademark Office*